United States Patent [19]

Hubbard

[11] Patent Number: 4,567,437
[45] Date of Patent: Jan. 28, 1986

[54] DUAL OSCILLATOR METHOD FOR DETECTING FLAWS IN A MOVING CHAIN

[76] Inventor: Lincoln W. Hubbard, 52 Parkview Ave., Warwick, R.I. 02805

[21] Appl. No.: 502,938
[22] Filed: Jun. 10, 1983
[51] Int. Cl.[4] .................. G01N 27/82; G01R 35/00
[52] U.S. Cl. ...................... 324/237; 324/61 QS; 324/202; 331/65
[58] Field of Search ............. 324/202, 234, 236, 237, 324/327, 61 QS, 61 QL; 331/46, 56, 65, 64; 340/551

[56] References Cited

U.S. PATENT DOCUMENTS

| | | | |
|---|---|---|---|
| 2,806,181 | 9/1957 | Rockafellow | 324/236 X |
| 2,919,413 | 12/1959 | Charles | 324/327 X |
| 3,201,774 | 8/1965 | Vemura | 324/327 X |
| 3,521,184 | 7/1970 | Bowker | 324/236 X |
| 3,543,145 | 11/1970 | Dufayet | 324/237 |
| 3,727,075 | 4/1973 | Buckley et al. | 331/65 X |
| 3,745,451 | 7/1973 | Goyette | 324/237 X |
| 3,854,084 | 12/1974 | Parker | 324/234 |
| 3,986,104 | 10/1976 | Randolph | 324/327 |
| 4,195,260 | 3/1980 | Sakamoto et al. | 324/236 |

FOREIGN PATENT DOCUMENTS 2011086  7/1979  United Kingdom ............... 324/236

*Primary Examiner*—Gerard R. Strecker
*Attorney, Agent, or Firm*—Barlow & Barlow

[57] ABSTRACT

A method of detecting a flaw in a moving chain is disclosed in which two identical free-running oscillators are used, and through the inductive core of one a chain is passed. A comparator circuit monitors the oscillators' outputs so that changes in mass of the chain may be sensed.

1 Claim, 2 Drawing Figures

DUAL OSCILLATOR METHOD FOR DETECTING FLAWS IN A MOVING CHAIN

BACKGROUND OF THE INVENTION

This invention relates to a mass detector and is particularly useful in detecting whether or not a link is missing from a chain, such as a jewelry chain.

If a link is missing in a chain such as a jewelry chain, this will result in a faulty product, which is normally sold in fairly long lengths. In addition, if a link is missing, it may indicate a faulty operation of the chain-making machine. Originally, detection of a missing link was accomplished through the visual observance of an operator, and of course, was subject to human error. It also required the stationing of a person in a position to view the output of the machine. With the advent of small gold jewelry chain, it became necessary in the industry to operate the machines continuously in order to produce sufficient output for the consumer demand. Some of the devices that have been used to automatically detect a missing link in a chain have comprised a single oscillator with the chain passing through the coil that is part of the resonant circuit, which was adjusted in such a way that if a link was missing, the normally inoperative oscillator would go into oscillation and activate a visual detection and/or automatic machine-stopping mechanism. An example of a device of this general nature is seen in the Buckley et al patent, U.S. Pat. No. 3,727,075. One of the difficulties that has been found utilizing oscillators of this nature that go in and out of oscillation is that they are not stable, and the mass passing through the inductor, or the lack thereof, may not always be detected due to the inability of the oscillator to trigger itself on and off.

SUMMARY OF THE INVENTION

It is an object of this invention to provide a simple and automatic mass detector circuit apparatus which is stable in operation and is impervious to such external effects as temperature and stray magnetic fields.

According to the principal aspect of the invention, there is provided a pair of oscillator circuits mounted on a common board in reasonable proximity to each other, each having tank circuit means which include an inductor; one inductor through which the moving mass such as chain may pass, while the other inductor has a brass moveable core. The oscillator with the moveable core is adjusted so that its output is made slightly greater than the output of the oscillator with the chain inserted within the core so that the comparator into which the oscillator outputs are fed, will give a zero output. A change in the mass within the core of where the chain passes will create a change in the inductive reactance which will be sensed by the comparator and cause an output at the comparator that may actuate an indicator and a controlled device.

Essentially, therefore, the instant invention provides a method of detecting a flaw in a moving mass such as chain in which two oscillators are provided, each having a reactive component in a frequency determining circuit, then placing a chain in the field of one reactive component of a first oscillator, comparing the amplitude output of the two oscillators, and then adjusting the reactive component of the second oscillator to bring the amplitude to slightly greater than the amplitude of the first oscillator so that there will be zero output of a comparator circuit. The output of the comparator is monitored as an indication of the absence or presence of a flaw in the moving chain, which in effect is the absence or presence of mass. Preferably, the output of each of the oscillators is rectified and smoothed to a direct current component before being compared.

The foregoing and other objects, features and advantages of the invention will be apparent from the following description.

DESCRIPTION OF THE PREFERRED EMBODIMENT

Figure 1:
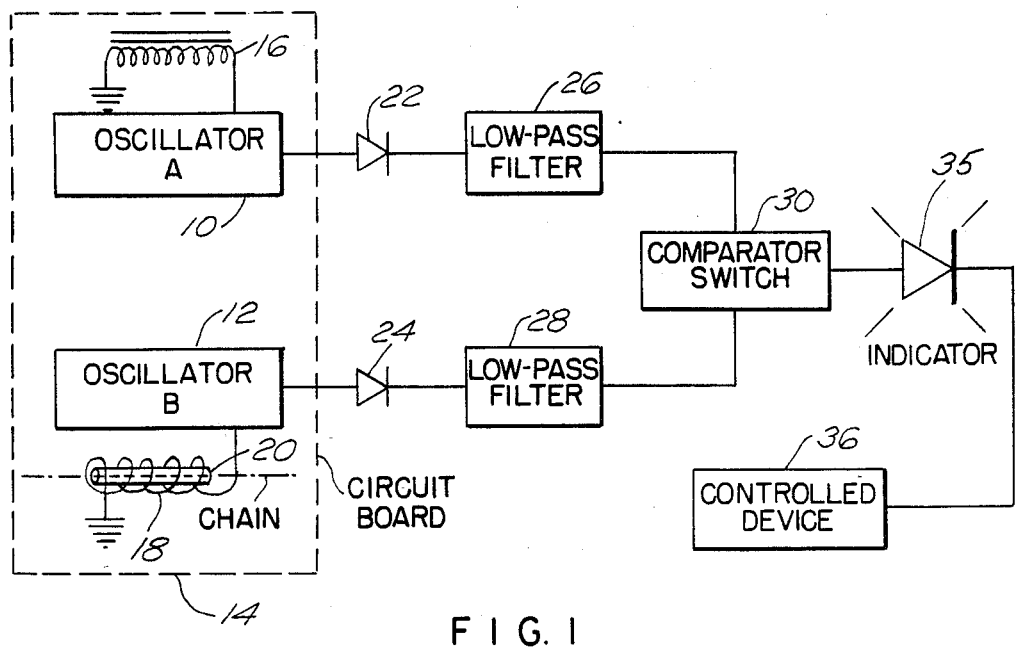
FIG. 1 is a block diagram of the apparatus of the present invention.

In FIG. 1 two oscillators 10 and 12 are shown, each of which is mounted on a common circuit board 14 and each of which includes at least in the frequency determining circuit, an inductance, there being shown an inductance 16 for oscillator 10 and an inductance 18 for oscillator 12. Within inductance 16 is a brass adjustable core seen diagrammatically in the circuit, and within the inductance 18 is a tubular member 20 through which the part to be tested may pass; in this case the part is a continuous chain. The output of each oscillator is rectified as by rectifiers 22, 24; and then passes through a low pass filter 26, 28 so that essentially a smoothed DC component is achieved that is then fed to a comparator 30.

Essentially to this point, the two oscillators 10 and 12 which are mounted on the same circuit board to be in the same environment, are running full time in their oscillatory mode. It has been found satisfactory to operate the oscillators in the two or three mHz region and mount the inductive component of each of the oscillator circuits at opposite ends of the circuit board so as to reduce any chance of coupling therebetween, as each oscillator is a free-running unit of its own. Best results are obtained by matching the components of the frequency determining circuit. Initially, therefore, for set-up, a good chain will be placed through the tube 20 and the brass core of resonant circuit 16 will be adjusted so that the amplitude output of oscillator 10 is slightly greater than the amplitude output of oscillator 12. To insure that the device is operating correctly, a faulty chain with a link missing may be placed within the tube 20 and the core is readjusted to the same output as before; the position of the brass core within the inductor 16 is noted again, and the brass core is now placed in between these two adjustment points. This adjusts the threshold of the circuit so that an actuation will take place whenever a faulty link of a chain is passed through the core 20. If, however, there is a change in the output between oscillator A and oscillator B caused by a faulty chain, then the difference in the signal appearing at the output of the low pass filters will be noted on the comparator and an indicator, such as an indicator 35, seen as a light emitting diode, may illuminate; and in addition, a controlled device such as 36 can be actuated due to the output from the comparator switch 30.

Figure 2:
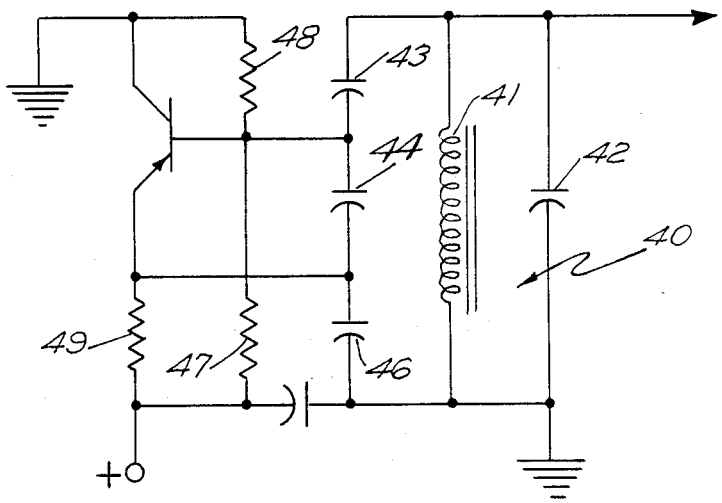
FIG. 2 is a detailed schematic of a preferred oscillator circuit used in connection with the apparatus.

Referring now to FIG. 2, there is illustrated for convenience, a preferred circuit for the oscillators A and B seen diagrammatically as an indicated 10 and 12. To this end, there is shown the tank circuit 40 having an inductor 41 and a parallel capacitor 42. Across the tank circuit is a capacitive voltage divider, including a feedback capacitor 43 and divider capacitors 44 and 46. Proper base voltage is established by voltage divider resistors 47, 48, the emitter being supplied with voltage through dropping resistor 49; and the collector is grounded. It will be apparent that the size of the feedback capacitor 43, which feeds back oscillatory energy to the emitter, must be sized so that in effect the resonant circuit is lightly loaded. This can be likened to a one-turn link on a resonant circuit, it being desired not to swamp the oscillator, but to keep the same lightly loaded. For example, with very small jewelry chain, it has been found advantageous to use, as example for capacitor 43, 36 pf; for capacitor 46, 130 pf; and for capacitor 44, 220 pf. In effect, capacitors 44 and 43 are sufficiently large to swamp out any reactive changes in the tank circuit and further limit harmonic output to enchance frequency stability. If, however, it becomes necessary to measure larger chain, then several items will change; and for example, the coupling capacitor could readily be increased in value as will the value increase for capacitor 46. In addition, the inductance 41 will change since larger wire will be used, and the inductance will decrease, it having been found that, for example, the inductances for small wire wound on a small bobbin can amount to approximately 15 mH, while for larger wire, they will amount to approximately 5 mH.

I claim:

1. A method of detecting a flaw in a moving chain comprising the steps of providing two oscillators with ringing circuits having capacitive and inductive components; placing a brass core in the inductive component of the first oscillator; placing a perfect chain in the other inductive component; adjusting the oscillatory amplitude of the first oscillator to be slightly greater than the other oscillator; noting the position of the brass core; replacing the perfect chain with a faulty chain and readjusting the brass core to the same output as before; noting the new position of the brass core and adjusting the core to a position between the noted positions to establish a threshold signal for a faulty chain; removing the faulty chain; providing a comparator and feeding the output of the two oscillators to the comparator; passing a moving chain through the said other inductive component to check for flaws whereby a faulty chain will cause a different output of the two oscillators and an output of the comparator as an indicator of the presence of a faulty chain.

* * * * *